(12) United States Patent
Fischer

(10) Patent No.: US 9,028,408 B2
(45) Date of Patent: May 12, 2015

(54) DETECTION DEVICE FOR THE DETECTION OF A BLOOD COUNT PARAMETER

(75) Inventor: Georg Fischer, Nuremberg (DE)

(73) Assignees: eesy-id GmbH, Graefelfing (DE); Friedrich-Alexander-Universitaet Erlangen-Nuernberg, Erlangen (DE)

( * ) Notice: Subject to any disclaimer, the term of this patent is extended or adjusted under 35 U.S.C. 154(b) by 180 days.

(21) Appl. No.: 13/884,377

(22) PCT Filed: Oct. 28, 2011

(86) PCT No.: PCT/EP2011/069034
§ 371 (c)(1),
(2), (4) Date: Jul. 17, 2013

(87) PCT Pub. No.: WO2012/069282
PCT Pub. Date: May 31, 2012

(65) Prior Publication Data
US 2013/0303868 A1 Nov. 14, 2013

(30) Foreign Application Priority Data
Nov. 24, 2010 (EP) .................................... 10192473

(51) Int. Cl.
*A61B 5/145* (2006.01)
*A61B 5/05* (2006.01)

(52) U.S. Cl.
CPC ........... *A61B 5/0507* (2013.01); *A61B 5/14532* (2013.01); *A61B 5/14542* (2013.01)

(58) Field of Classification Search
USPC .................................. 600/309, 310, 316, 365
See application file for complete search history.

(56) References Cited

U.S. PATENT DOCUMENTS

| 6,332,087 | B1 | 12/2001 | Svenson et al. |
| 2008/0200790 | A1 | 8/2008 | Kim et al. |
| 2009/0312615 | A1* | 12/2009 | Caduff et al. ................. 600/316 |
| 2010/0069731 | A1 | 3/2010 | Harra et al. |
| 2010/0112614 | A1* | 5/2010 | Axelrod et al. ................. 435/14 |

FOREIGN PATENT DOCUMENTS

| WO | WO-2007003955 A1 | 1/2007 |
| WO | WO-2010105373 A1 | 9/2010 |

OTHER PUBLICATIONS

International Search Report for PCT/EP2011/069034 dated May 12, 2011.

* cited by examiner

*Primary Examiner* — Eric Winakur
(74) *Attorney, Agent, or Firm* — Marshall, Gerstein & Borun LLP

(57) ABSTRACT

A detection device for detecting a blood count parameter in a blood vessel, comprising a transmitter having a number of transmit antennas for transmitting at least one transmit signal, a receiver having a number of receive antennas for receiving at least one receive signal, a processor to select a detection configuration comprising one of the transmit antennas and one of the receive antennas and select a second detection configuration comprising one of the transmit antennas and one of the receive antennas, and a loss detector that is designed, when the first detection configuration is selected to transmit a transmit signal, to detect a first loss value on the basis of the transmit signal and a receive signal, and, when the second detection configuration is selected to transmit a transmit signal, detect a second loss value on the basis of the transmit signal and a receive signal. The processor is designed to select the detection configuration having the lower loss value to detect the blood count parameter.

25 Claims, 21 Drawing Sheets

| Diam. El | A | B | C | D | E | F | G |
|---|---|---|---|---|---|---|---|
| 6 mm | <1 | +2 | -1 | -9 | -17 | +11 | <1 |
| 3.4 mm | -1 | +4 | -1 | -13 | | | -10 |

DETECTION DEVICE FOR THE DETECTION OF A BLOOD COUNT PARAMETER

BACKGROUND OF THE INVENTION

1. Field of the Invention

The present invention relates to the field of detecting a concentration of a blood constituent, for example sugar in blood flowing through a blood vessel.

2. Related Technology

In order to ascertain a blood picture parameter, such as, for example, a concentration of a blood constituent, blood can be taken invasively. The blood picture parameter can then be ascertained using the taken blood by means of standardized test strips, the electric resistance values of which depend on the concentration of the blood constituent, e.g. blood sugar. By way of example, the respective electric resistance value can be detected using a blood sugar measuring instrument, which carries out a DC current resistance measurement for detecting an electric resistance value of a test strip. The resistance value can be converted into a blood sugar concentration on the basis of a relationship, known per se, between a blood sugar concentration and a resistance value. In order to obtain high detection accuracy, each test strip is provided with calibration data, for example with a reference resistance value or with a corresponding code, as a result of which variations of properties of the test strips can be compensated for. However, a disadvantage of invasive methods is the necessity of taking blood and hence of injuring a patient. Moreover, continuous detection of a concentration of a blood constituent, for example to establish the diurnal variation curve thereof, is complicated. Furthermore, it is not possible to detect a time delay between food being taken and, for example, an increase in the blood sugar accurately by means of the invasive method. Also, particularly in the case of a low concentration of the blood sugar in blood, the time for administering insulin to the patient cannot be ascertained accurately.

For noninvasive ascertaining of a blood picture parameter such as, for example, a substance concentration or a substance composition in the blood, use can be made of microwave-spectroscopic methods. Microwave spectroscopy for detecting blood picture parameters is based on coupling a microwave signal into tissue perfused by blood and detecting a frequency-dependent absorption of coupled-in microwave energy.

The article "Non-invasive glucose monitoring in patients with Type 1 diabetes: A multi-sensor system combining sensors for dielectric and optical characterization of skin", Biosensors and Bioelectronics 24 (2009) 2778-2784 by Andreas Caduff et al. describes a multi-electrode arrangement for microwave-based ascertaining of a blood picture parameter. The multi-electrode arrangement comprises a plurality of electrode pairs with different electrode spacings, by means of which different penetration depths of microwave signals can be realized. The blood picture parameter is detected by means of an impedance measurement, i.e. by means of a one-port measurement, and is therefore susceptible to errors in the case of possible impedance maladjustments. As a result of different penetration depths, it is sometimes not possible to distinguish between capillary and venous blood, which can falsify the measurement results. In general, a measurement of a blood picture parameter using venous blood is more precise than a measurement of the blood picture parameter using capillary blood because, for example, blood sugar changes in capillary blood are delayed compared to venous blood.

The articles "A microwave frequency sensor for non-invasive blood-glucose measurement", SAS 2008-IEEE Sensors Applications Symposium, Atlanta, Ga., Feb. 12-14, 2008, by Buford Randal Jean et al. and "Calibration methodology for a microwave non-invasive glucose sensor", Master's Thesis, Baylor University, May 2008 by M. McClung describe a further electrode arrangement for ascertaining a blood sugar concentration. What is exploited here is that the dielectric properties of blood depend on a blood sugar content. By pressing a thumb onto the microwave sensor, a change in the relative permittivity of the thumb is measured by a detuning of a resonator. However, blood is displaced by the contact pressure of the thumb, and this can lead to falsification of the measurement results. Moreover, the measurements cannot be carried out continuously. The evaluation of the measurement data for ascertaining the blood sugar content moreover depends on the respective patient and is therefore not reproducible in other patients. Moreover, this method does not allow control of the penetration depth of the microwave power, and so it is not possible to distinguish between capillary and venous blood. Furthermore, the change in the relative permittivity is carried out on the basis of a one-port measurement, which is susceptible in respect of maladjustments.

SUMMARY OF THE INVENTION

The invention provides a more accurate method for detecting a blood picture parameter, for example a concentration of blood sugar in blood.

The invention provides a detection device for detecting a blood picture parameter of blood in a blood vessel, comprising:

a transmitter with a number of transmission antennas for emitting at least one transmission signal;

a receiver with a number of reception antennas for receiving at least one reception signal;

a processor configured to select a first detection configuration comprising one transmission antenna of the number of transmission antennas and one reception antenna of the number of reception antennas and to select a second detection configuration comprising one transmission antenna of the number of transmission antennas and one reception antenna of the number of reception antennas;

a loss detector, which is configured, if the first detection configuration for emitting a transmission signal is selected, to detect a first loss variable on the basis of the transmission signal and a reception signal and, if the second detection configuration for emitting a transmission signal is selected, to detect to detect a second loss variable on the basis of the transmission signal and a reception signal; wherein the processor is configured to select the detection configuration with the smaller loss variable for detecting the blood picture parameter.

The invention further provides a method for detecting a blood picture parameter of blood in a blood vessel, using a transmitter with a number of transmission antennas for emitting at least one transmission signal and a receiver with a number of reception antennas for receiving at least one reception signal, comprising the following steps:

selecting a first detection configuration comprising selection a transmission antenna of the number of transmission antennas and a reception antenna of the number of reception antennas;

if the first detection configuration for emitting a transmission signal is selected, detecting a first loss variable on the basis of the transmission signal and a reception signal, selecting a second detection configuration comprising a transmission antenna of the number of transmission antennas and a reception antenna of the number of reception antennas;

if the second detection configuration for emitting a transmission signal is selected, detecting a second loss variable on the basis of the transmission signal and a reception signal; and selecting the detection configuration with the smaller loss variable for detecting the blood picture parameter.

The present invention is based on the discovery that a blood picture parameter can be ascertained precisely on the basis of microwaves if the microwaves are coupled directly into the blood vessel such that the blood picture parameter can be ascertained on the basis of the venous blood.

To this end, use is made of the further discovery that a blood vessel, the fatty tissue surrounding the latter and a layer of skin can be considered to be a dielectric waveguide system, in which both transverse electric and transverse magnetic waves are able to propagate. In order to realize a targeted coupling of microwaves into the blood vessel, provision can be made, for example, for a number of transmission antennas on the transmission side and a number of reception antennas on the reception side. By means of a permutation of all antenna combinations, it is possible, for example, to select that antenna pair comprising a transmission antenna about a reception antenna which is connected with the smallest coupling-in losses. The selected antenna pair can then be used for microwave-based detection of the blood picture parameter.

In accordance with one aspect, the invention relates to a detection device for detecting a blood picture parameter of blood in a blood vessel, comprising a transmitter with a number of transmission antennas for emitting at least one transmission signal, a receiver with a number of reception antennas for receiving at least one reception signal, a processor, which is configured to select a first detection configuration comprising one transmission antenna of the number of transmission antennas and one reception antenna of the number of reception antennas and to select a second detection configuration comprising one transmission antenna of the number of transmission antennas and one reception antenna of the number of reception antennas, a loss detector, which is configured, if the first detection configuration for emitting a transmission signal is selected, to detect a first loss variable on the basis of the transmission signal and a reception signal and, if the second detection configuration for emitting a transmission signal is selected, to detect a second loss variable on the basis of the transmission signal and a reception signal, wherein the processor is configured to select the detection configuration with the smaller loss variable for detecting the blood picture parameter.

The transmission signals are preferably emitted in the direction of the blood vessel. On the basis of the reception signals, which are received versions of the transmission signals, and on the basis of the transmission signals it is possible, for example, to select that pair of antennas, comprising a transmission antenna and a reception antenna, as that detection configuration which is connected with the smallest coupling-in losses. The coupling-in losses can, for example, be detected on the basis of a comparison of the aforementioned loss variables, for example absorption lines or attenuations.

In accordance with one embodiment, if the first detection configuration is selected, the transmitter is configured to emit the transmission signal by means of the transmission antenna of the first detection configuration, wherein, if the first detection configuration is selected, the receiver is configured to receive the reception signal by means of the reception antenna of the first detection configuration, wherein, if the second detection configuration is selected, the transmitter is configured to emit the transmission signal by means of the transmission antenna of the second detection configuration, and wherein, if the second detection configuration is selected, the receiver is configured to receive the reception signal by means of the reception antenna of the second detection configuration, and wherein the loss detector is configured to detect the first loss variable on the basis of the transmission signal and the reception signal of the first detection configuration and to detect the second loss variable on the basis of the transmission signal and the reception signal of the second detection configuration.

In accordance with one embodiment, the processor is configured to compare the first loss variable with the second loss variable in order to ascertain the smaller loss variable of the two loss variables.

In accordance with one embodiment, the detection device comprises a switching matrix, in particular a switching matrix which can be controlled by the processor, which switching matrix is configured to connect respectively one output of a reception antenna of the number of reception antennas with the loss detector.

In accordance with one embodiment, the transmitter comprises a transmission signal generator, wherein one output of the transmission signal generator can be connected to respectively one transmission antenna of the number of transmission antennas by means of a switching matrix, in particular by means of a switching matrix which can be controlled by the processor.

In accordance with one embodiment, the transmitter is configured to emit transmission signals of the same frequency, in particular a frequency in a frequency range between 1 GHz and 15 GHz, or of the same mode or of the same wave type, in particular a transverse electric mode or a transverse magnetic mode, when the first detection configuration is selected and when the second detection configuration is selected.

In accordance with one embodiment, the transmitter comprises at least two transmission antennas, with the receiver comprising at least two reception antennas. The transmission antennas and the reception antennas can be dipole antennas or frame antennas or patch antennas.

In accordance with one embodiment, the loss detector comprises a network analyzer, in particular a scalar or vector network analyzer, or a power detector.

In accordance with one embodiment, in order to detect the blood picture parameter, the transmitter is configured, using the transmission antenna of the selected detection configuration, to couple a first transmission signal with a first frequency and a second transmission signal with a second frequency into the blood vessel. The receiver is configured, using the reception antenna of the selected detection configuration, to receive a first reception signal at the first frequency and a second reception signal at the second frequency. The loss detector is configured to ascertain a first loss variable on the basis of the first transmission signal and the first reception signal at the first frequency and to ascertain a second loss variable on the basis of the second transmission signal and the second reception signal at the second frequency. The processor is configured to ascertain a first frequency shift of the first loss variable relative to a first reference loss variable, to establish a second frequency shift of the second loss variable relative to a second reference loss variable and to establish the blood picture parameter on the basis of the first frequency shift and the second frequency shift.

In accordance with one embodiment, in order to detect the blood picture parameter, the transmitter is configured, using the transmission antenna of the selected detection configuration, to couple a first transmission signal with a first frequency and a second transmission signal with a second frequency into the blood vessel. The receiver is configured, using the reception antenna of the selected detection configuration, to receive a first reception signal at the first frequency and a second reception signal at the second frequency. The processor is configured to establish a first electric loss variable on the basis of the first transmission signal and the first reception signal, to establish a second electric loss variable on the basis of the second transmission signal and the second reception signal, to ascertain a relaxation time constant of a blood constituent depending on the frequency with the larger electric loss variable, and to establish the blood picture parameter on the basis of a pre-known relationship between the relaxation time constant and the blood picture parameter.

In accordance with one embodiment, the loss detector is configured, in order to ascertain the first loss variable and the second loss variable, to carry out a two-port measurement, in particular to ascertain in each case a forward transmission factor $S_{21}$ by means of the two-port measurement.

In accordance with one embodiment, the loss detector is configured to ascertain the first loss variable and the second loss variable respectively on the basis of the following formula:

$$P_{loss} = 1 - |S_{11}|^2 - |S_{21}|^2,$$

where $P_{loss}$ denotes the respective loss variable and where $S_{11}$ denotes the input reflection factor and $S_{21}$ denotes the forward transmission factor.

In accordance with one embodiment, the transmitter is configured to couple in the transmission signal as a mode or a wave type, in particular as a transverse electric (TE) wave or a transverse magnetic (TM) wave or a transverse electromagnetic (TEM) wave or an HE wave, in particular to couple it in tangentially or transversely with respect to an extent of the blood vessel or with respect to the blood flow direction.

In accordance with one embodiment, the blood picture parameter is a concentration of a blood constituent, in particular a sugar such as glucose, or of lactate or of lactic acid or of oxygen.

In accordance with a further aspect, the invention relates to a method for detecting a blood picture parameter of blood in a blood vessel, using a transmitter with a number of transmission antennas for emitting at least one transmission signal and a receiver with a number of reception antennas for receiving at least one reception signal, comprising the following steps: selecting a first detection configuration comprising selection a transmission antenna of the number of transmission antennas and a reception antenna of the number of reception antennas, if the first detection configuration for emitting a transmission signal is selected, detecting a first loss variable on the basis of the transmission signal and a reception signal, selecting a second detection configuration comprising a transmission antenna of the number of transmission antennas and a reception antenna of the number of reception antennas, if the second detection configuration for emitting a transmission signal is selected, detecting a second loss variable on the basis of the transmission signal and a reception signal, and selecting the detection configuration with the smaller loss variable for detecting the blood picture parameter.

Further method steps emerge directly from the functionality of the detection device.

BRIEF DESCRIPTION OF THE DRAWINGS

Further exemplary embodiments will be explained with reference to the attached figures. In detail.

DETAILED DESCRIPTION

Figure 1:
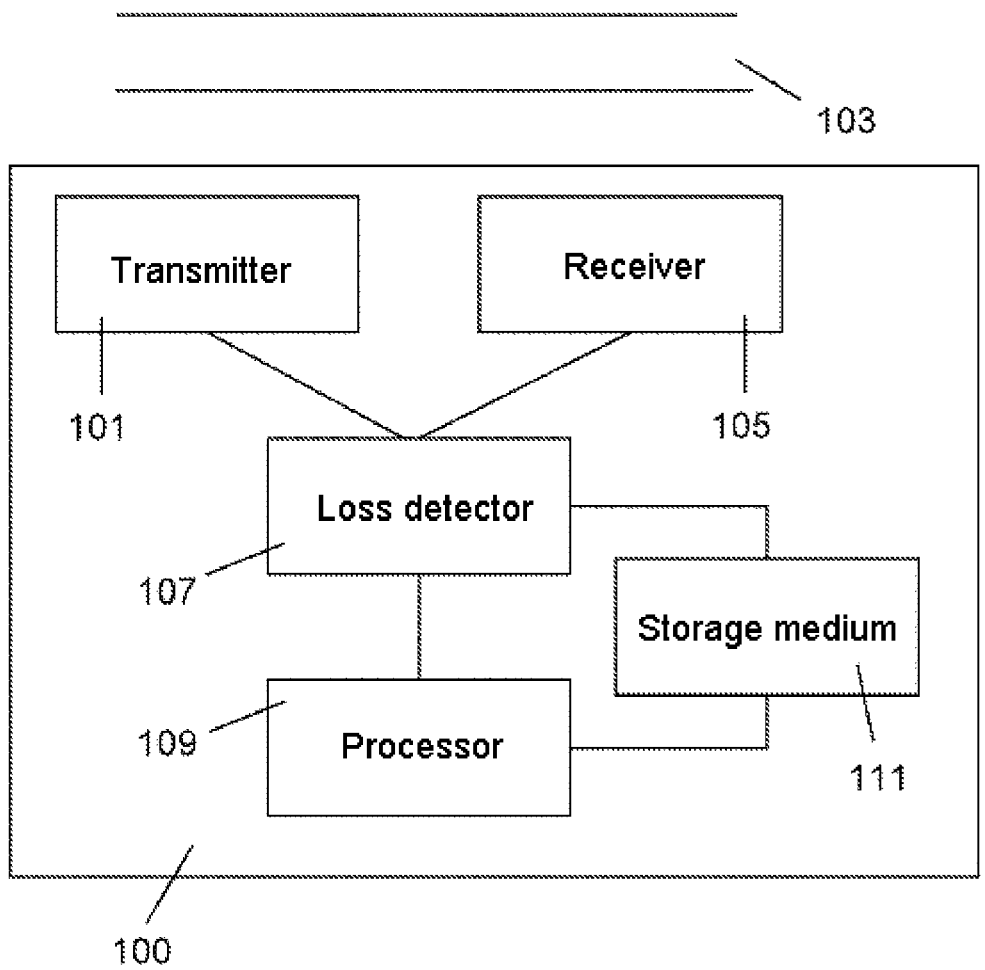
FIG. 1 shows a block diagram of a detection device.

FIG. 1 shows a block diagram of a detection device 100 for detecting a blood picture parameter such as, for example, a concentration of blood sugar. The detection device comprises a transmitter 101, which is configured to couple at least one transmission signal, for example a microwave signal, into the blood vessel 103 illustrated schematically in FIG. 1.

The detection device 100 furthermore comprises a receiver 105, which is configured to receive at least one reception signal.

The detection device 100 furthermore comprises a loss detector 107, which can, for example, comprise a power detector. The loss detector 107 is coupled to the transmitter 101 and to the receiver 105.

The detection device furthermore comprises a processor 109, which is coupled to the loss detector 107.

The detection device 100 can optionally have a storage medium 111, which, for example, the processor 109 and, optionally, the loss detector 107 can access.

The transmitter 101 can, for example, have one or more transmission antennas for emitting one or more transmission signals, which antennas can, for example, be configured as dipole antennas or frame antennas or patch antennas. Analogously to this, the receiver 105 can have one or more transmission antennas for receiving one or more reception signals. The processor 109 is preferably configured to select a plurality of detection configurations in succession. Here, each detection configuration comprises a single transmission antenna and a single reception antenna, wherein the transmission antennas can be spaced apart from one another and wherein the reception antennas can be spaced apart from one another. When a detection configuration is selected, the transmitter 101 excites the associated transmission antenna to emit a transmission signal, with the receiver 105 using the respective reception antenna to receive a reception signal.

The loss detector 107 can, for example, ascertain an electromagnetic loss variable such as energy absorption on the basis of the transmission signal and the reception signal. In the next step, a further detection configuration is used for emitting a transmission signal and a further loss variable is detected. This is how a plurality of detection configurations are used in succession, or in any sequence, to couple a transmission signal into the blood vessel 103, with a loss variable being ascertained by means of the loss detector 107 in each detection configuration. By way of example, the processor 109 can compare the loss variables and select that detection configuration which is connected with the smallest loss variable. The selected detection configuration is used for detecting the blood picture parameter, as described below.

Figure 2:
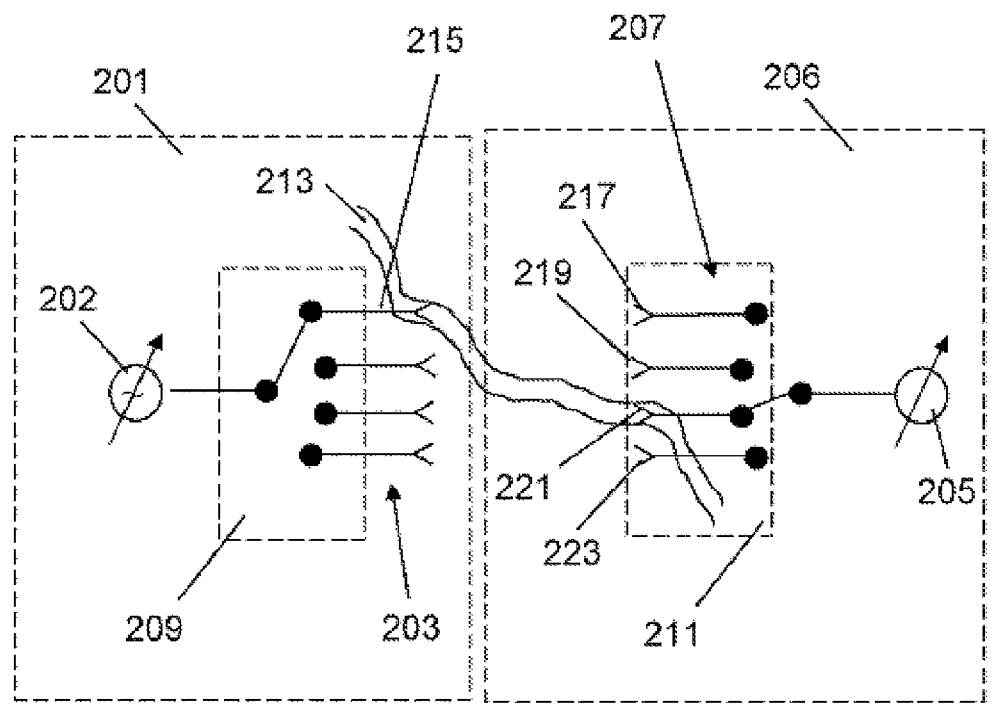
FIG. 2 shows a block diagram of a detection device.

FIG. 2 shows a detection device, which can be an embodiment of the detection device 100 illustrated in FIG. 1. The detection device comprises a transmitter 201, which can, for example, have a tunable oscillator 202, and a plurality of transmission antennas 203. The detection device furthermore comprises a loss detector 205, which can, for example, have a power detector. Furthermore, provision is made for a receiver 206 with a plurality of reception antennas 207.

One output of the tunable oscillator 202 can be connected to each antenna input, for example in succession or in any sequence, in a switchable manner, for example by means of a switching matrix 209. Analogously to this, each output of a reception antenna of the plurality of reception antennas 207 can be connected to the loss detector 205 by means of a switching matrix 211.

The switching matrices 209, 211 can have switches, in particular transistor switches.

By way of example, the switching matrix 211 and the switching matrix 209 can be used to select that pair comprising a transmission antenna and a reception antenna which enables optimum coupling of a microwave signal into a blood vessel 213 illustrated schematically in FIG. 2. The switching matrices 209 and 211 are used to select the antenna pairs in succession, starting with, for example, a first transmission antenna 215 by means of which a transmission signal is emitted.

On the reception side, the switching matrix 211 is used to select the reception antennas in succession, starting with, for example, the reception antenna 217 for receiving a corresponding reception signal, with a loss variable being detected on the basis of the transmission signal and the reception signal. In the next step, the reception antenna 219 is for example selected, with a loss variable once again being detected by means of the loss detector on the basis of the transmission signal and a reception signal received by the reception antenna 219. After this, for example, the reception antenna 221 is selected, with a further loss variable being detected on the basis of the transmission signal and a reception signal. In the next step, the reception antenna 223 is selected and a further loss variable is ascertained on the basis of the transmission signal and a reception signal received by the reception antenna 223. In the next step, the switching matrix 209 can, for example, select a further transmission antenna, wherein the aforementioned steps can be repeated. By a comparison of the established loss variables, the smallest loss variable, for example, is established. In the example illustrated in FIG. 2, it is to be expected, for example, that the detection configuration with the transmission antenna 215 and the reception antenna 221 is afflicted with the smallest coupling-in losses because the antennas 215, 221 lie directly above the blood vessel and therefore enable a signal to be coupled into the blood vessel 213. By way of example, the selected detection configuration can be used for detecting a blood picture parameter. The above-described selection steps can be carried out in any sequence. Thus, for example, all or some of the reception antennas 207 can be tested for the transmission antenna 215.

The transmission antennas 203 or the reception antennas 207 can differ in respect of their location and/or in respect of their field component which should be excited in a dominant fashion. Here, the switching matrices 209 and 211 ensure that the optimal excitation type, for example a loop antenna, an electric dipole antenna, a patch antenna, or excitation location can be selected for the respectively selected frequency.

By way of example, the detection device illustrated in FIG. 2 can be integrated in an inflatable armband. Between the detections of the loss variables, which can, for example, take place by measuring the control parameters, air can be allowed to escape from the armband such that the skin is aerated and no sweat is formed. A time interval between the measurements can be variable in this case. By way of example, the measurements can be carried out at intervals of 10 minutes. However, depending on requirements, more frequent measurements can be carried out, wherein the frequency of the measurements can be ascertained, for example, by the times when the meals are taken.

Since the transmission or reception antennas, which lie on the skin and can respectively be formed by an electrode plate, can slip, particularly in the pauses between the measurements, the selection of a plurality of excitation means illustrated in FIG. 2 can ensure that an excitation means which lies over the blood vessel 213 is selected. Hence that excitation means which enables a maximum of coupling microwave energy into the blood vessel 213 can be selected by means of the respective switching matrix 209 and 211.

In the following text, ascertaining the blood picture parameter is described in an exemplary fashion on the basis of the detection device 100 illustrated in FIG. 1. However, the explanations below also apply analogously to the detection device illustrated in FIG. 2.

In order to ascertain the blood picture parameter, the transmitter 101 can, in accordance with one embodiment, for example the blood vessel 103 illustrated schematically in FIG. 1, couple in a first transmission signal with a first frequency and a second transmission signal with a second frequency. By way of example, the first transmission signal and the second transmission signal can together result in a broadband signal. The transmitter 101 can be configured to emit the first transmission signal and the second transmission signal after one another, for example by means of a frequency sweep. To this end, the transmitter 101 can have one or more transmission antennas, which can, for example, be embodied as dipole antennas or frame antennas or patch antennas.

The detection device 100 furthermore comprises the receiver 105, which can be configured to receive a first reception signal at the first frequency and a second reception signal at the second frequency. To this end, the receiver can have one or more reception antennas.

The detection device 100 furthermore comprises the loss detector 107, which can, for example, be coupled to the transmitter 101 and the receiver 105 and can be provided for ascertaining a first loss variable on the basis of the first transmission signal and the first reception signal and also a second loss variable on the basis of the second transmission signal and the second reception signal.

The detection device 100 furthermore comprises the processor 109, which can be coupled to the loss detector 107 and can be provided for ascertaining a first frequency shift of the first loss variable relative to a first reference loss variable and a second frequency shift of the second loss variable relative to a second reference loss variable. The processor 109 can furthermore be configured to ascertain the blood picture parameter on the basis of the two frequency shifts.

The detection device 100 can furthermore have the storage medium 111, which can be accessed by, for example, the processor 109 and, optionally, the loss detector 107. By way of example, the first and the second reference loss variable or a plurality of reference loss variables are stored in the storage medium 111. By way of example, the reference loss variables can be absorptions or absorption lines of a water solution with a blood constituent, for example blood sugar. The loss variables detected on the basis of the frequency shifts can be frequency-shifted absorptions or absorption lines such that the blood picture parameter, such as, for example, a concentration of blood sugar, can be established on the basis of the frequency shifts.

The detection device 100 illustrated in FIG. 1 or in FIG. 2 uses the discovery that a blood vessel, a layer of skin and fatty tissue surrounding the blood vessel of, for example, a human forearm can be considered to be a dielectric waveguide system. The makeup of a human forearm is described in, for example, Netter, F. N. "Atlas der Anatomie" [Anatomical Atlas], Thieme Verlag, 2006. A human forearm consists of two bones which are surrounded by muscular tissue. Distributed around the muscular tissue are surface veins, i.e. blood vessels. The bones, the muscular tissue and the veins are encapsulated by fatty tissue, which is covered by upper layers of skin. The surface veins are arranged relatively close to the upper layers of skin and separated therefrom by the fatty tissue. By way of example, if the transmitter 101 and the receiver 105, illustrated in FIG. 1, are placed onto the upper layer of skin, the transmitter 101 can be used to couple e.g. a transverse electric (TE) wave or a transverse magnetic (TM) wave into the dielectric waveguide system formed by a blood vessel, fatty tissue and a layer of skin. Here, the layer of skin and the fatty tissue can be understood to be a thin-film waveguide.

By way of example, if use is made of a microwave measurement head, as can be employed for ascertaining a complex relative permittivity of materials, it is possible thereby to characterize the substance mixture consisting of skin, fatty tissue and veins.

In order to detect a blood picture parameter, it is advantageous to detect substantially only the venous blood. To this end, the transmitter 101 can be configured to couple the transmission signal in the form of an electromagnetic wave directly into the blood vessel 103. The transmitter 101 and the receiver 105 can each have a plurality of antennas such that, for the purposes of coupling the electromagnetic wave into the blood vessel and decoupling an electromagnetic wave from the blood vessel 103, it is in each case possible to select that transmission antenna and reception antenna which are connected with the smallest coupling losses.

Figures 3A, 3B, 3C:
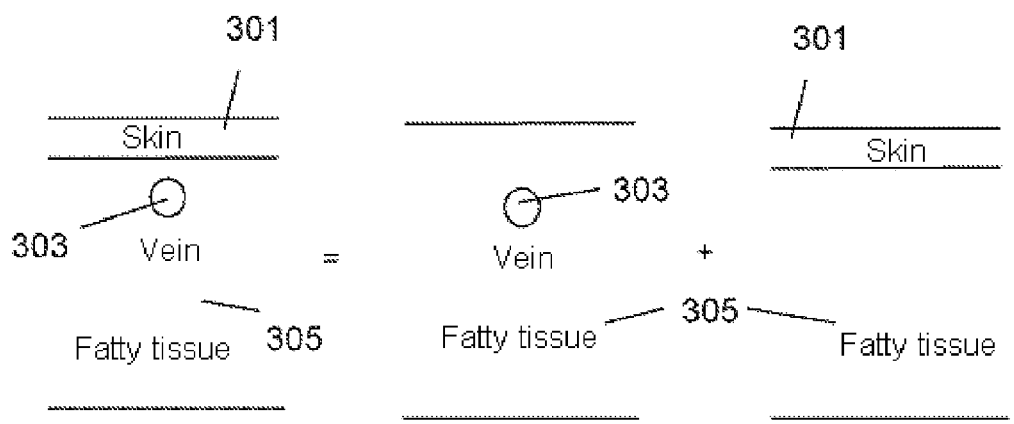
FIG. 3 shows a model of a cross-section of a human forearm.

FIGS. 3A to 3C illustrate a simplified model of a cross-section of a human forearm, e.g. of a wrist, as can be employed, for example, for field simulations or for modeling a dielectric waveguide system. As illustrated in FIG. 3A, the model comprises a layer of skin 301, a blood vessel 303 and fatty tissue 305 surrounding the blood vessel 303, e.g. a vein. The model illustrated in FIG. 3A forms a dielectric waveguide system comprising the dielectric waveguide illustrated in FIG. 3B and the electrical thin-film waveguide illustrated in FIG. 3C.

The dielectric waveguide illustrated in FIG. 3B comprises the blood vessel 303 and the fatty tissue 305 surrounding the latter. By contrast, the dielectric thin-film waveguide from FIG. 3C comprises the layer of skin 301 and the fatty tissue 305. A different dispersive, i.e. frequency dependent, behavior of the respective complex relative permittivity can be attached in each case to the layer of skin 301, to the fatty tissue 305 and to the blood vessel 303. Here, the blood vessel 303 lying at the top is interpreted as a dielectric waveguide, in which, depending on the frequency, different modes or wave types, for example a TE wave, a TM wave, a TEM wave or an HE wave, are able to propagate. Added to the waveguide mechanism in the dielectric waveguide, there is an additional waveguide mechanism in the form of the thin-film waveguide illustrated in FIG. 3C, which is formed by the upper layer of skin 301.

A transmission antenna of the transmitter 101 and a reception antenna of the receiver 105 can preferably be configured in such a way that they couple microwave power into the blood vessel 303 in a dedicated fashion and decouple said microwave power again after, for example, a few centimeters. Here, the blood vessel 303 serves as a measurement length and should therefore be considered as a distributed element and no longer as a concentrated element. The measurement of the loss variables is preferably carried out on the basis of a two-port measurement. Here, particularly when coupling the detection device to a wrist, primary modes can be excited in the dielectric waveguide 3B such that an excitation of thin-film waveguide modes in the thin-film waveguide 3C is avoided, as a result of which the blood picture parameter can be detected more accurately.

In order to excite primary modes in the dielectric waveguide system, it is possible to take into account that, depending on the selected frequency of a transmission signal, different modes can be dominant. It is preferable for mode types, which have a concentration of the fields in the blood vessel 303, to be preferred over those modes in which the fields are concentrated in the layer of skin 301. What is shown on the basis of the dielectric properties of the dielectric waveguide illustrated in FIG. 3B is that for certain types of modes longitudinal components $E_{longitudinal}$, $H_{longitudinal}$ are stronger in the propagation direction, i.e. in the direction of a blood vessel extent, than the transverse components $E_{transverse}$, $H_{transverse}$, i.e. transverse to the blood vessel extent. Therefore those modes which enable maximum coupling of the microwave power into the blood vessel 303 are preferably excited in the frequency range to be detected.

FIGS. 4A to 4D illustrate some antennas in an exemplary fashion, which antennas can be used as transmission antennas, i.e. excitation means, or else as reception antennas.

Figure 4A:
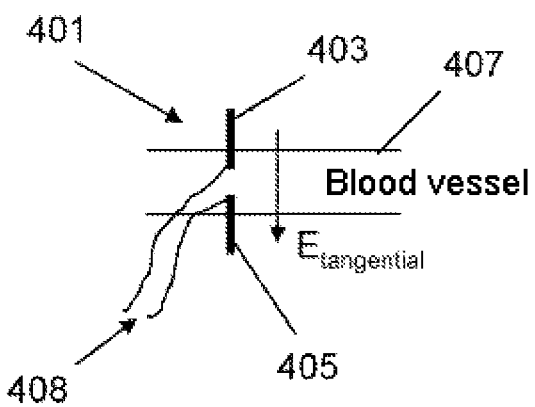
FIGS. 4A to 4D show antennas.

The antenna 401 illustrated in FIG. 4A is configured as an electric dipole with a first antenna section 403 and a second antenna section 405. The antenna sections 403 and 405 are distanced from one another and are arranged, for example, transversely with respect to the extent of a blood vessel 407. The antenna 401 can be excited by supply lines 408. An electric dipole arranged in this manner can, for example, generate an electric field $E_{tangential}$, which points across the extent of the blood vessel or across the blood flow direction.

Figure 4B:
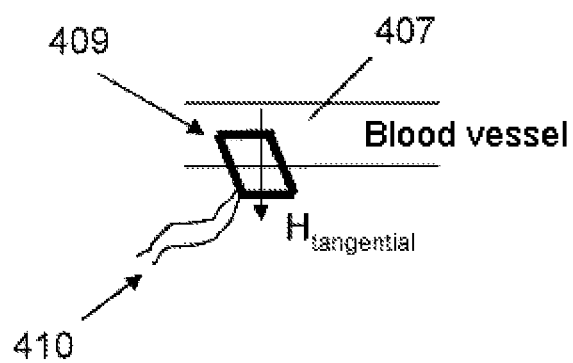

FIG. 4B illustrates an antenna 409, which can be a frame antenna. By way of example, the frame antenna can have a quadrilateral or round shape. In the arrangement of the frame antenna 409 with respect to the blood vessel 407 illustrated in FIG. 4B, e.g. a magnetic field $H_{tangential}$ is excited, which points across the extent of the blood vessel 407 or across the blood flow direction. The antenna 409 can be excited by supply lines 410.

Figure 4C:
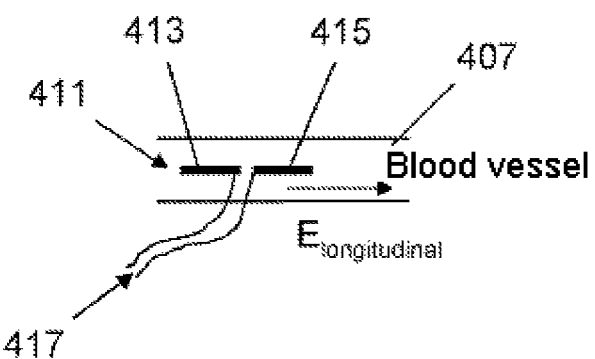

FIG. 4C illustrates an antenna 411, which forms an electric dipole with a first antenna section 413 and a second antenna section 415. The antenna sections 413 and 415 are distanced from one another and are excited by means of the supply lines 417 illustrated in FIG. 4C. The electric dipole formed by the antenna 411 is arranged in such a way with respect to the extent of the blood vessel 407 that the sections 413 and 415 are arranged parallel to the extent of the blood vessel 407. As a result of this, an electric field with the field component $E_{longitudinal}$, which electric field points in the direction of the extent of the blood vessel, is excited.

Figure 4D:
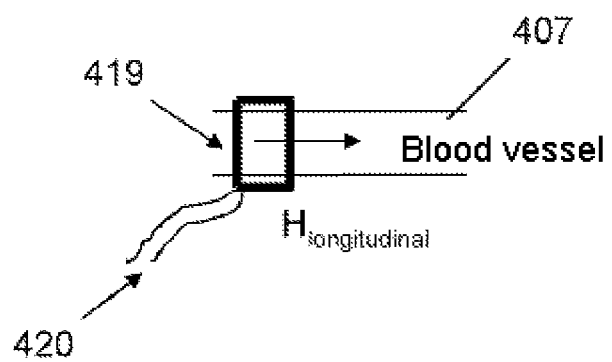

FIG. 4D shows a frame antenna 419, which can, for example, be formed in the form of a quadrilateral or round frame, which forms a loop antenna. The frame antenna 419 is excited by means of supply lines 320 and is, as illustrated in FIG. 4D, arranged in such a way with respect to the extent of the blood vessel 407 or with respect to the blood flow direction that the magnetic field has a component $H_{longitudinal}$ pointing in the direction of the extent of the blood vessel 407.

By way of example, the frequency range to be measured in each case conforms to which spectral lines, i.e. which absorption lines, should be detected. By way of example, it is possible to observe the characteristic absorption lines of a substance or else an effect which a specific blood constituent has on the absorption lines of water or of a water solution with a concentration of the blood constituent.

The antennas illustrated in FIGS. 4A to 4D are either electric dipoles or magnetic frame antennas. Moreover, use can also be made of patch antennas. Electric dipoles dominantly produce an electric field along the axis of the electric dipole. This axis can either, as illustrated in FIG. 4A, be aligned tangentially with respect to the blood vessel 407 or the blood flow direction or, as illustrated in FIG. 4C, be aligned in the direction of the blood vessel 407 or in the blood flow direction. If it is primarily a magnetic field that should be generated, a frame antenna can be used as excitation means. If a surface vector on the surface spanned by the frame forming the frame antenna is aligned across the blood vessel 407 or across the blood flow direction, the magnetic field is also aligned across the blood vessel 407, as illustrated in FIG. 4B. By contrast, if the surface vector points in the direction of the blood vessel 407, the magnetic field is also aligned in the direction of the blood vessel 407, as is illustrated in, for example, FIG. 4B. The selection of an excitation means illustrated in FIGS. 4A to 4D then results in, for example, the dominant excited mode or wave type.

Figure 5A:
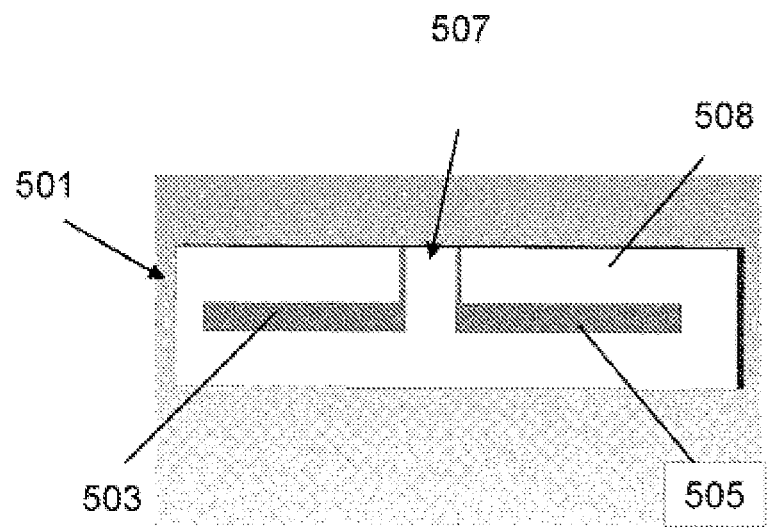
FIG. 5 shows an electric dipole antenna.
FIG. 5B shows an excitation arrangement.

FIG. 5A shows an electric dipole antenna 501, which can be used as a transmission antenna or as a reception antenna. The electric dipole antenna 501 comprises dipole antenna sections 503 and 505, which are arranged in or on a substrate 508 and can be excited by means of supply lines 507. The dipole antenna 501 can be used as a transmission antenna or as a reception antenna.

Figure 5B:
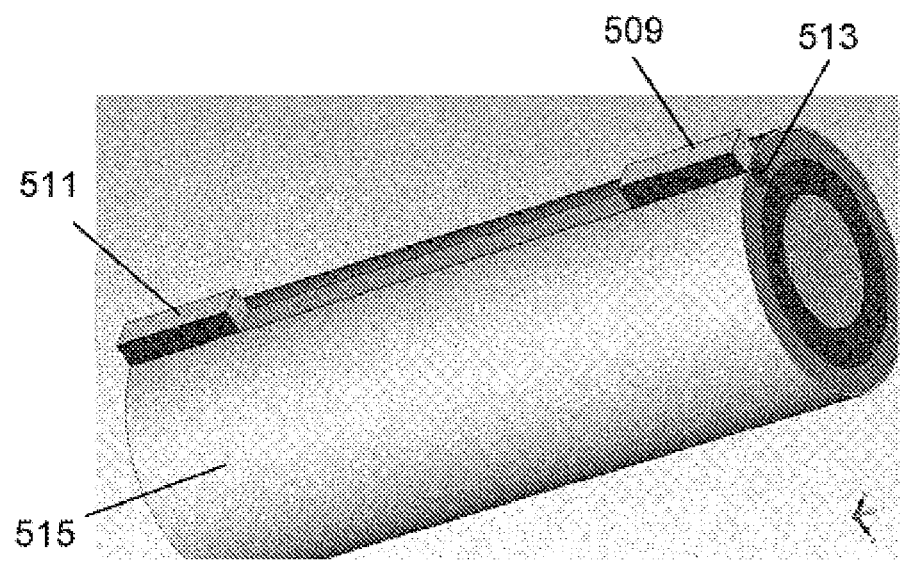

FIG. 5B shows an excitation arrangement of a transmission antenna 509 of a transmitter and of a reception antenna 511 of a receiver in the direction of an extent of a blood vessel 513 below a layer of skin 515. The transmission antenna 509 and the reception antenna 511 are, for example, electric dipole antennas in accordance with FIG. 5A. In the arrangement illustrated in FIG. 5B, an electric field with a field component in the direction of the extent of the blood vessel 513, or in the blood flow direction, is generated.

Figure 6A:
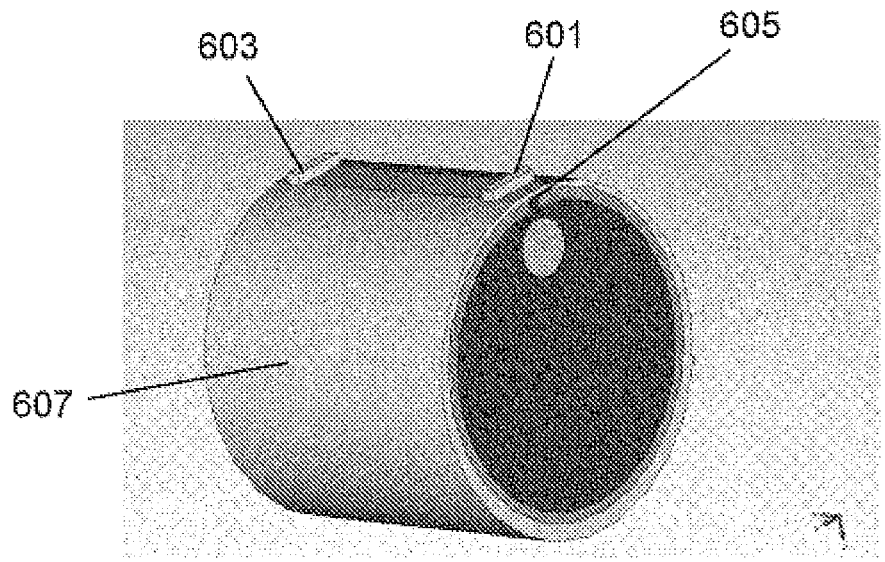
FIGS. 6A, 6B show excitation arrangements.
Figure 6B:
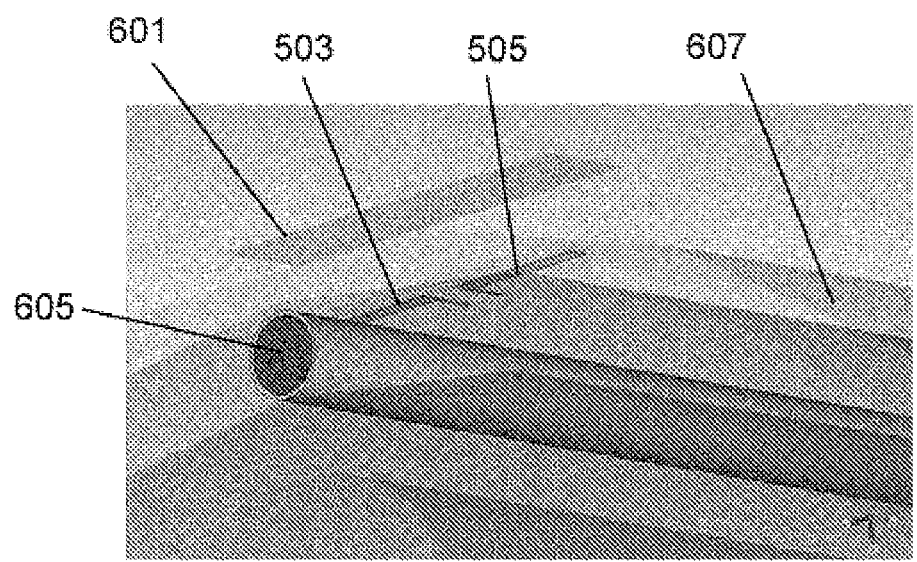

FIG. 6A shows an excitation arrangement comprising a transmission antenna 601 of a transmitter and a reception antenna 603 of a receiver, across the direction of extent of a blood vessel 605, i.e. across the blood flow direction, which lies under a layer of skin 607. The transmission antenna 601 and the reception antenna 603 can each be formed by e.g. the electric dipole antenna illustrated in FIG. 5A. In FIG. 6B, the arrangement of the dipole antenna sections 503 and 505 is illustrated in more detail in respect of the blood flow direction.

Figure 7A:
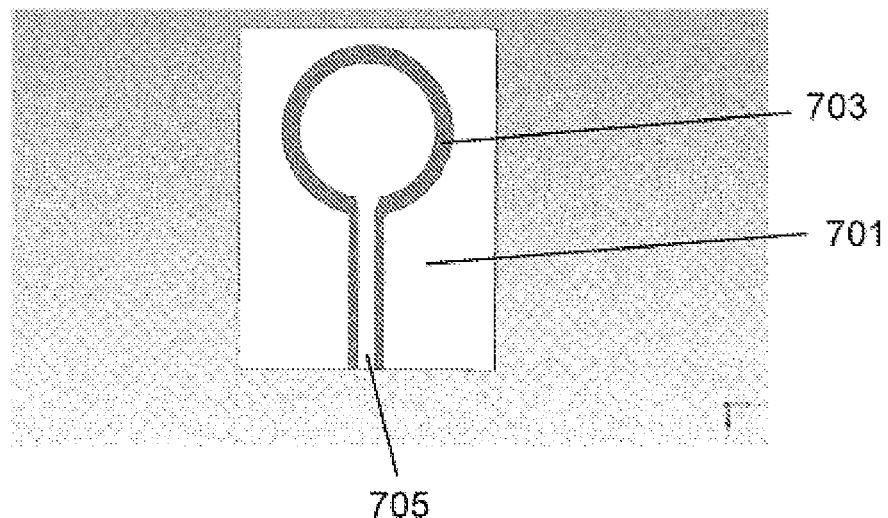
FIG. 7A shows a loop antenna 601.

FIG. 7A shows a loop antenna 701 with a circular frame 703 and supply lines 705 for exciting the circular frame 703. The loop antenna 701 can, for example, be used as a transmission antenna or as a reception antenna. The circular frame 703 and the supply lines 705 can be arranged in or on a substrate.

Figure 7B:
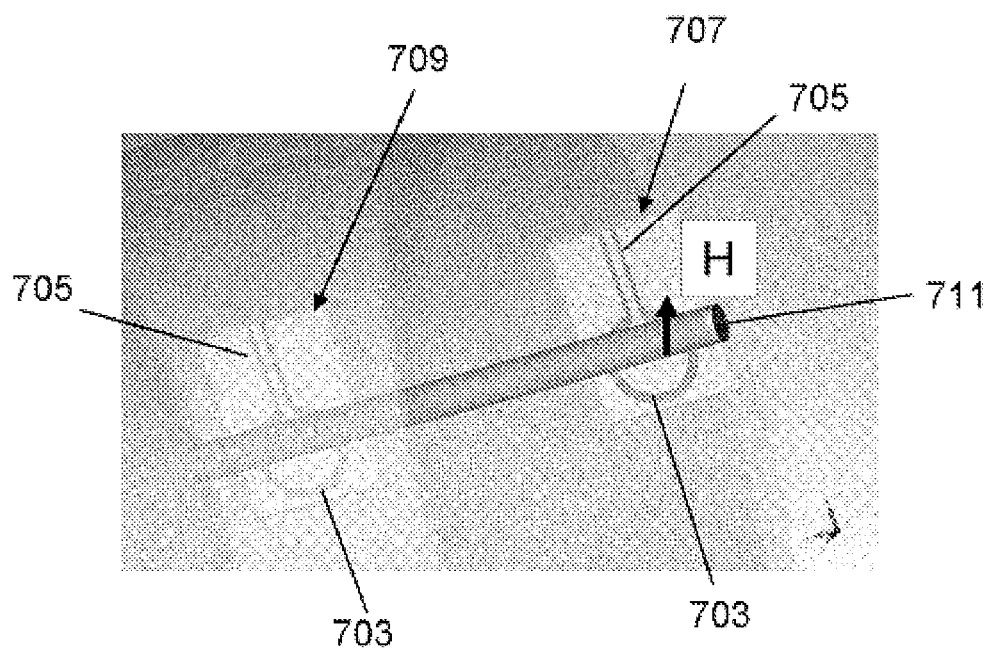
FIG. 7B shows an excitation arrangement.

FIG. 7B shows an excitation arrangement with a transmission antenna 707 of a transmitter and a reception antenna 709 of a receiver, which can be formed as loop antennas as per FIG. 7A. By way of example, the loop antennas 707, 709 are arranged in such a way that the circular frames 703 are arranged above a blood vessel 711, with the supply lines 705 pointing across the extent of the blood vessel 711, i.e. across the blood flow direction. As a result of this, a magnetic field with a component H of the magnetic field pointing across the extent of the blood vessel 711 is generated on the transmitter side.

Figure 8:
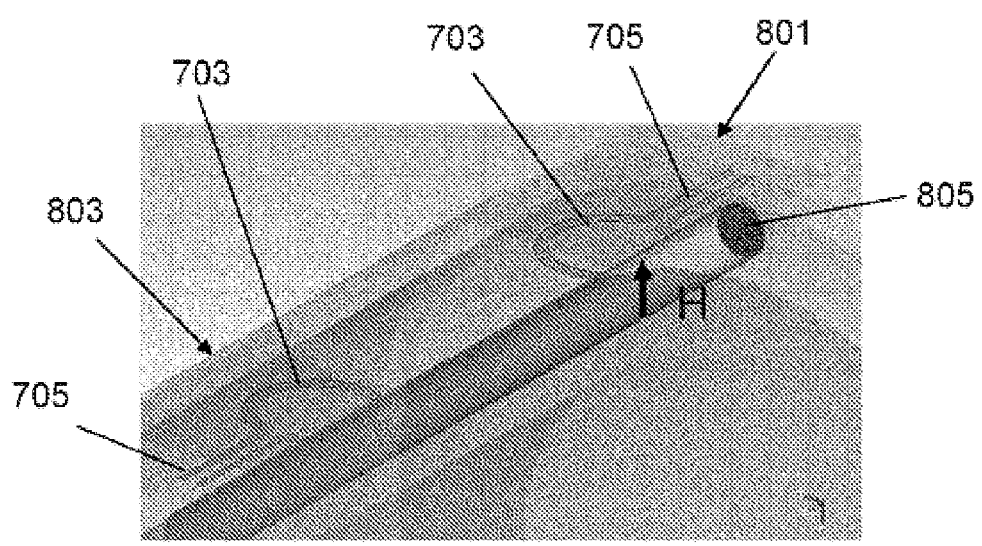
FIG. 8 shows an excitation arrangement.

FIG. 8 shows an excitation arrangement of a transmission antenna 801 of a transmitter and a reception antenna 803 of a receiver, with respect to a blood vessel 805. By way of example, the transmission antenna 801 and the reception antenna 803 can be loop antennas with that shape illustrated in FIG. 7A. By way of example, they are arranged in such a way that the circular frames 703 are respectively arranged above the blood vessel 705 and that the supply lines 705 extend pointing away from one another, parallel to the extent of the blood vessel 805. As a result of this, a magnetic field component H pointing perpendicular to the extent of the blood vessel 805 is generated, which magnetic field component points in the direction of a normal of the surface spanned by the circular frame 803.

Figure 9:
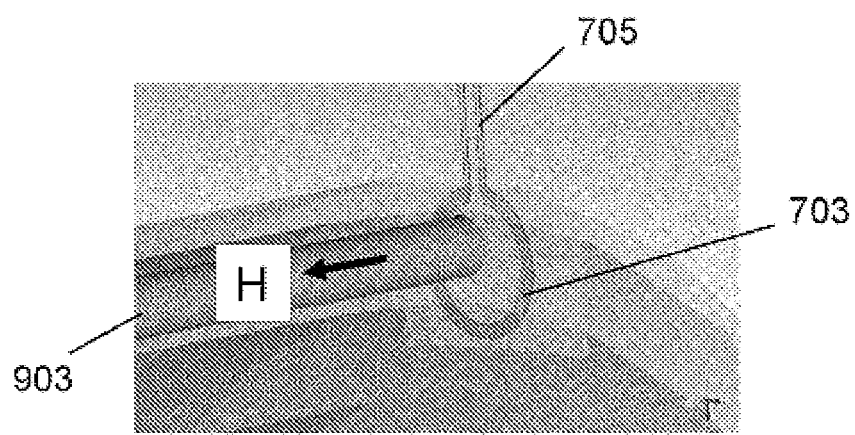
FIG. 9 shows an excitation arrangement.

FIG. 9 shows an excitation arrangement with a transmission antenna 901 of a transmitter, which, for example, has the shape of a loop antenna illustrated in FIG. 7A. By way of example, the transmission antenna 901 is arranged in such a way with respect to a blood vessel 903 that a normal of the surface spanned by the frame 703 points in the direction of the extent of the blood vessel 903. By way of example, such an arrangement can be realized at a bend of the blood vessel 903. As a result of this, a magnetic field component H pointing in the direction of the extent of the blood vessel 903 is generated.

Figure 10:
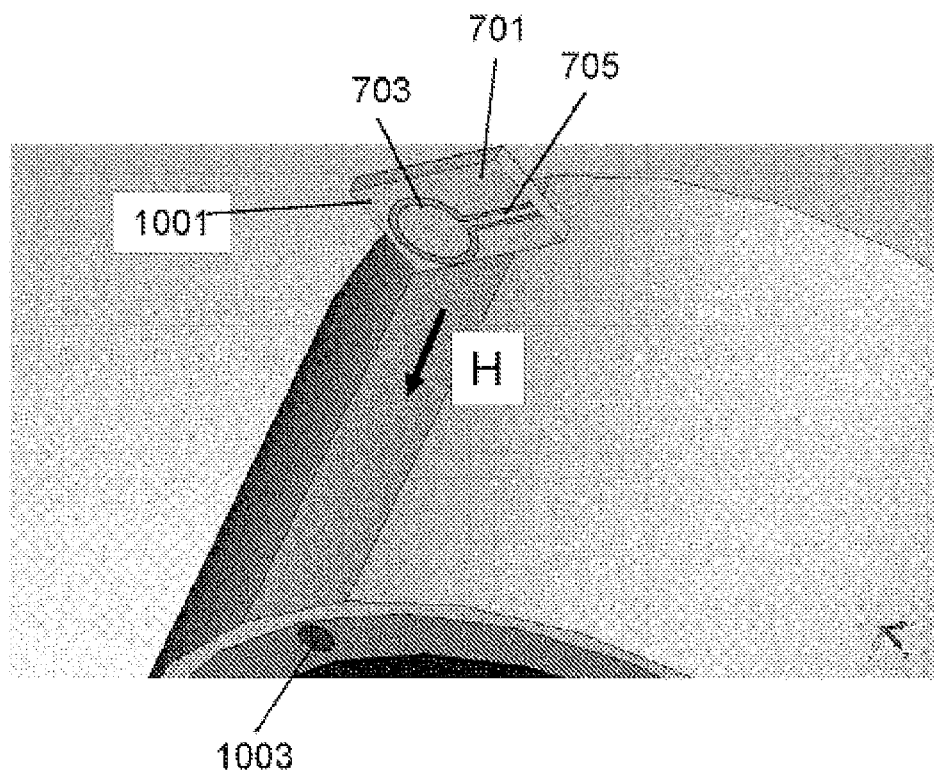
FIG. 10 shows an excitation arrangement.

FIG. 10 shows an excitation arrangement with a transmission antenna 701, which, for example, is a loop antenna with the shape illustrated in FIG. 7A and can be arranged in a substrate 1001, for example a polymer substrate. The transmission antenna 701 is arranged above a blood vessel 1003 in such a way that a normal of the surface spanned by the circular frame 703 points in the direction of the extent of the blood vessel 1003. As a result of this, a magnetic field is generated with a field component H pointing in the direction of the extent of the blood vessel 1003, i.e. in the blood flow direction.

Figure 11:
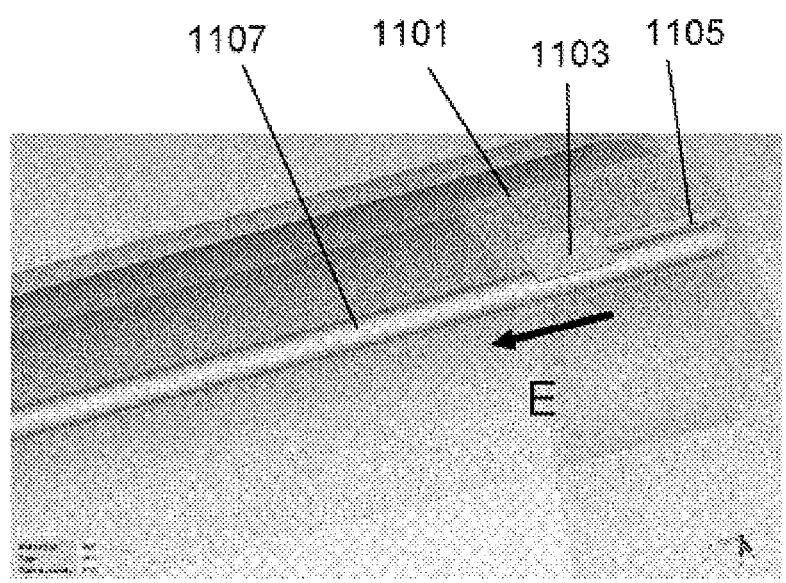
FIG. 11 shows an excitation arrangement.

FIG. 11 shows an excitation arrangement with a transmission antenna 1101, which can be a patch antenna with a patch antenna surface 1103 and supply lines 1105. The patch antenna surface 1103 is, for example, arranged above a blood vessel 1107, as a result of which an electric field is generated with an electric field component E pointing in the direction of an extent of the blood vessel 1107, i.e. in the blood flow direction.

In accordance with one embodiment, the loss detector 107 is configured to carry out e.g. a scalar or a vector measurement or a power measurement. In order to determine the loss variables, a simple spectroscopic measurement can be carried out, in which the absolute value of the measurement parameter S21 is detected.

Figure 12:
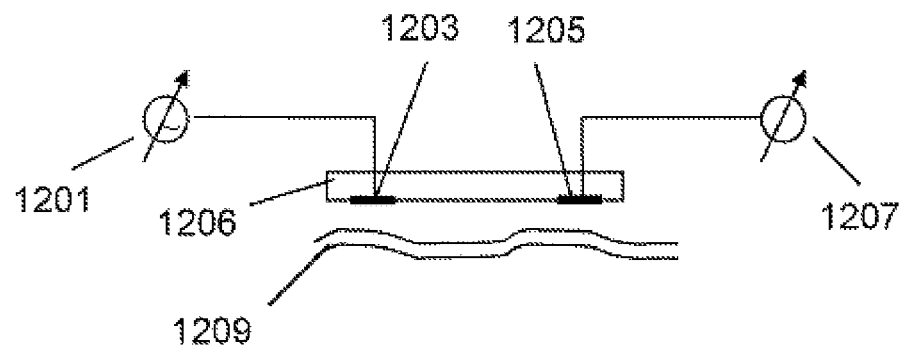
FIG. 12 shows a basic circuit diagram of a detection device.

By way of example, $|S_{21}|$ can be measured by means of the detection device illustrated in FIG. 12. The detection device comprises a transmitter with a transmission signal generator 1201, which can be a tunable oscillator. An output of the transmission signal generator 1201 is connected to a transmission antenna 1203. The detection device furthermore comprises a receiver with a reception antenna 1205, the output of which is connected to a loss detector 1207. By way of example, the loss detector can comprise a power detector. As illustrated in FIG. 12, the transmission antenna 1203 and the reception antenna 1205 are arranged above a blood vessel 1209. The transmitter can correspond to features of the transmitter 101, the receiver can correspond to features of the receiver 105 and the loss detector 1207 can correspond to features of the loss detector 107.

However, the accuracy when determining the loss variables, i.e. the losses in the waveguide, can be increased further by a further measurement of an absolute value of the measurement parameter S11. By way of example, the loss variables can be determined on the basis of the following formula:

$$P_{loss} = 1 - |S_{11}|^2 - |S_{21}|^2,$$

where $P_{loss}$ denotes the respective loss variable and where $S_{11}$ denotes the input reflection factor and $S_{21}$ denotes the forward transmission factor.

In order to detect the blood picture parameter, for example a concentration of blood sugar, frequency shifts of the absorption lines of a water solution with sugar can, for example, be examined.

Figure 13:
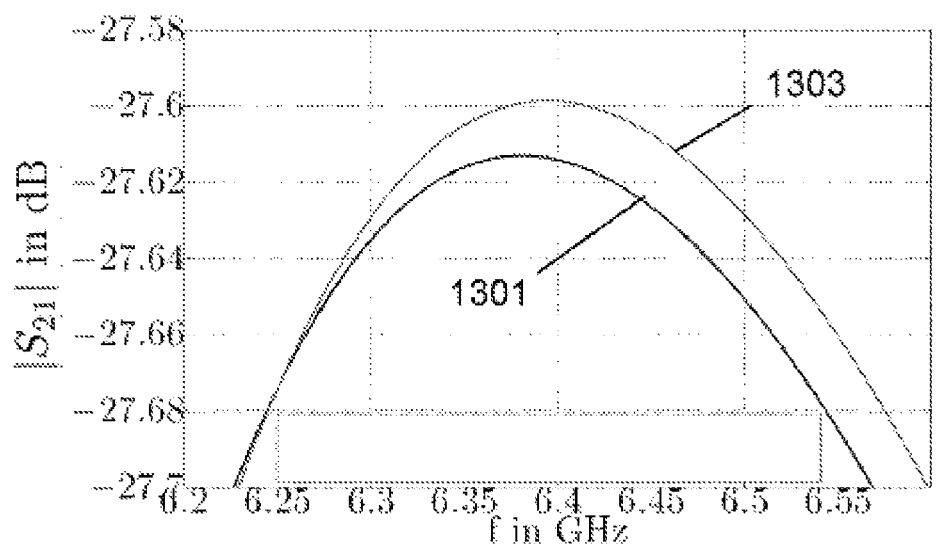
FIG. 13 shows a frequency shift of an absorption maximum.

By way of example, FIG. 13 shows a frequency shift of an absorption maximum 1401 at a first blood sugar concentration compared to a frequency shift of an absorption maximum 1403 at a second blood sugar concentration, which is higher than the first blood sugar concentration. Here, a transmission around 6 GHz was detected in an exemplary fashion as loss variable.

The frequency shift of the absorption maximum can be considered to be a measure for a blood picture parameter, for example for a blood sugar level. By observing frequency shifts in a number of absorptions of a water solution with sugar, the measurement reliability can be increased still further.

Figures 14, 15:
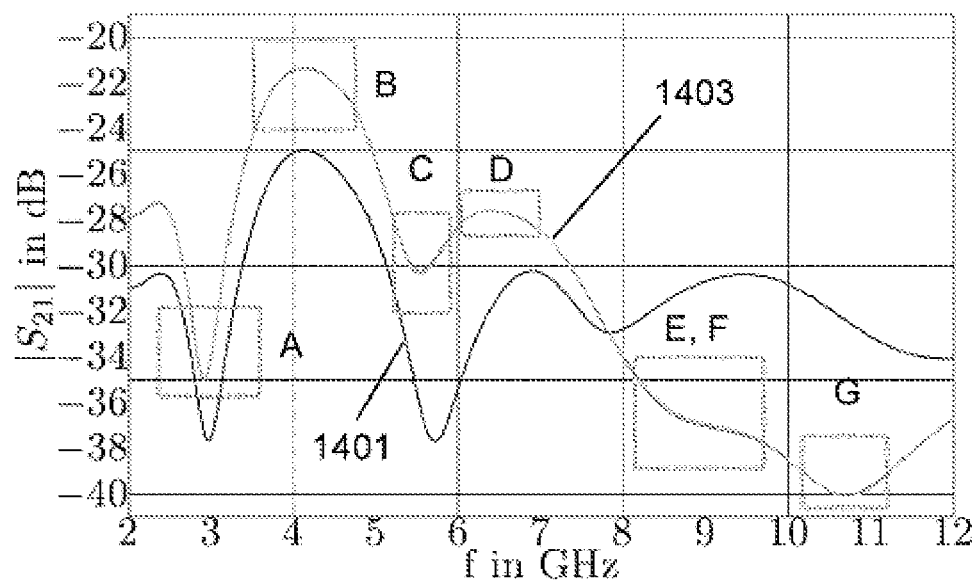
FIG. 14 shows a transmission behavior.
FIG. 15 shows frequency shifts.

FIG. 14 shows, in an exemplary fashion, a broadband transmission behavior of venous blood in a wrist. Here, the profiles 1401 and 1403 clarify different frequency positions of absorption lines at different blood sugar concentrations. In order to detect the blood picture parameter, such as, for example, the concentration of the blood sugar, it is possible, for example, to detect frequency shifts of the absorptions A, B, C, D, E, F and G in a targeted manner. Thus, it is possible, for example, to observe a shift in the direction of higher or lower frequencies depending on blood sugar level, for example in a frequency range between 2 GHz and 12 GHz, for each frequency of an absorption maximum and/or an absorption minimum.

FIG. 15 shows, in an exemplary fashion, frequency shifts of the absorptions A, B, C, D, E, F and G illustrated in FIG. 14 for a blood vessel with a diameter of 6 mm and for a blood vessel with a diameter of 3.4 mm. It is possible to identify that the absorptions for a sugar level variation can have frequency shifts in both positive and negative direction. Detecting a plurality of absorptions or absorption lines therefore makes it possible to detect a blood picture parameter, for example the blood sugar level, more accurately.

In accordance with one embodiment, the transmitter 101 of the detection device 100 shown in FIG. 1 can be embodied to couple a first transmission signal with a first frequency and a second transmission signal with a second frequency into the blood vessel 103 illustrated schematically in FIG. 1. By way of example, together, the first transmission signal and the second transmission signal can result in a broadband signal. The transmitter 101 can furthermore be configured to couple the first transmission signal and the second transmission signal, one after the other, into the blood vessel 103 in sequence. The receiver 105 can analogously be configured to receive a first reception signal at the first frequency and a second reception signal at the second frequency. The loss detector can be provided for ascertaining a first loss variable on the basis of the first transmission signal and the first reception signal and also a second loss variable on the basis of the second transmission signal and the second reception signal. The processor can be provided for ascertaining a relaxation time constant T of the blood picture parameter depending on the frequency with the greater loss variable. If further transmission signal and reception signal pairs are used, the loss detector 107 will accordingly establish further loss variables.

By way of example, the processor 109 will ascertain the relaxation time constant of the blood picture parameter depending on the first frequency if the first loss variable is greater than the second loss variable. Accordingly, the processor 109 will ascertain the relaxation time constant (i) of the blood picture parameter depending on the second frequency if the second loss variable is greater than the first loss variable. What is used here is the discovery that a blood picture parameter can be established by detecting the relaxation time constant of a blood constituent. By way of example, if the blood picture parameter to be determined is a concentration of blood sugar in blood, a relaxation time constant of a water solution containing sugar is a measure for the concentration of the blood sugar, i.e. for the blood sugar level.

Furthermore, the loss detector can be designed to establish the complex relative permittivity $\epsilon''$ for ascertaining the respective loss variable.

Figure 16:
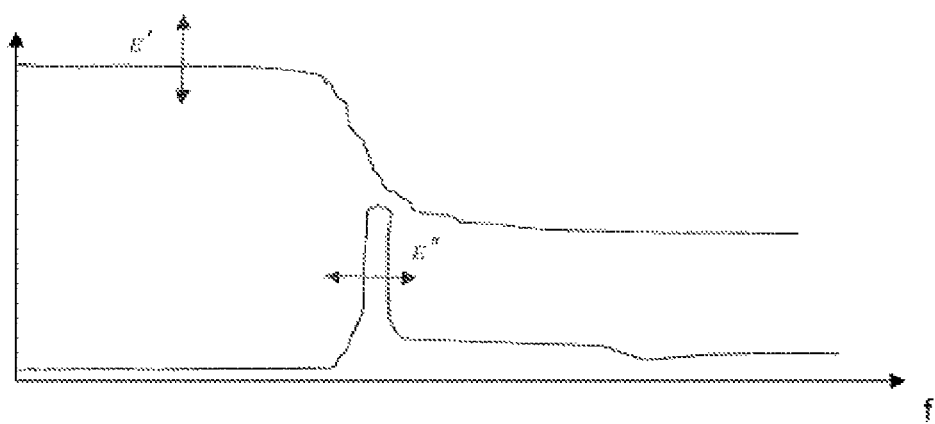
FIG. 16 shows a diagram for illustrating the real relative permittivity $\epsilon'$ and the complex relative permittivity $\epsilon''$ depending on the frequency.

To this end, FIG. 16 shows a diagram for illustrating the real relative permittivity $\epsilon'$ and the complex relative permittivity $\epsilon''$ depending on the frequency f.

Here, FIG. 16 illustrates that the losses represented by the complex relative permittivity $\epsilon''$ increase in the frequency range where the real part $\epsilon'$ transitions from the higher level to the lower level. These increases in the losses are also referred to as absorption lines in spectroscopy. The effect that can be used in this case is that the frequency at which the excesses of the losses—see local maximum of $\epsilon''$—is displaced with the concentration of the sugar content.

By way of example, the human body consists of 80% water. Water has absorption lines, for example at 19 GHz and 50 GHz. The detuning thereof can be ascertained and plotted against the sugar content. The detuning of the resonant frequency at $\epsilon''$ is—as illustrated in FIG. 16—easier to detect than the change in the plateau of $\epsilon'$. In particular, variations in the coupling advantageously do not shift the frequency of the maximum of $\epsilon''$. As a result, ascertaining the sugar concentration by observing $\epsilon''$ is significantly less susceptible to errors than observing $\epsilon'$ or the level change therein.

Since such curves as in FIG. 16 are superimposed in a multiplicity of substances, a separation of the substances by observing the imaginary relative permittivity $\epsilon''$ is easier to carry out since each substance can be associated with a specific absorption maximum. However, in the case of the real relative permittivity $\epsilon'$, it is only possible to observe the sum of all real relative permittivities $\epsilon'$ of all substances involved.

As already explained above, the processor 109 is configured to ascertain the relaxation constant T of the blood picture parameter depending on the frequency with the larger or maximum loss variable. Furthermore, the processor 109 is configured to establish the blood picture parameter, such as the glucose concentration in the blood, depending on the ascertained relaxation time constants.

Figure 17:
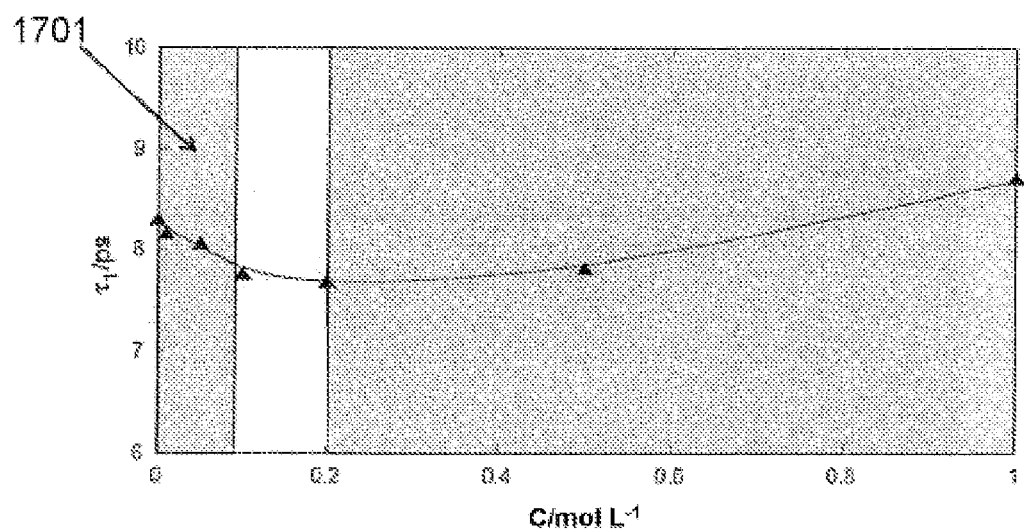
FIG. 17 shows a diagram for illustrating a relationship between the relaxation time constant ($\tau$) and the glucose concentration in the blood.

To this end, FIG. 17 shows a diagram for illustrating a relationship between the relaxation time constant (T) and the glucose concentration C/mol L$^{-1}$ in the blood. Here, the area denoted by the reference sign 1701 in FIG. 17 shows a critical blood sugar range.

Furthermore, the processor 109 is, in particular, configured to calculate the relaxation time constant (T) on the basis of the formula $$\tau = \frac{1}{2\pi f_A},$$

where $f_A$ denotes the frequency at which the established loss variable is at a maximum.

Advantageously, the processor 109 is then configured to ascertain the frequency at which the imaginary part of the complex relative permittivity $\epsilon''$ is at the maximum, and at which the relaxation time constant (T) is to be established depending on the ascertained frequency. This ascertained frequency is then used by the processor 109 for ascertaining the blood picture parameter, such as the glucose concentration.

Figure 18:
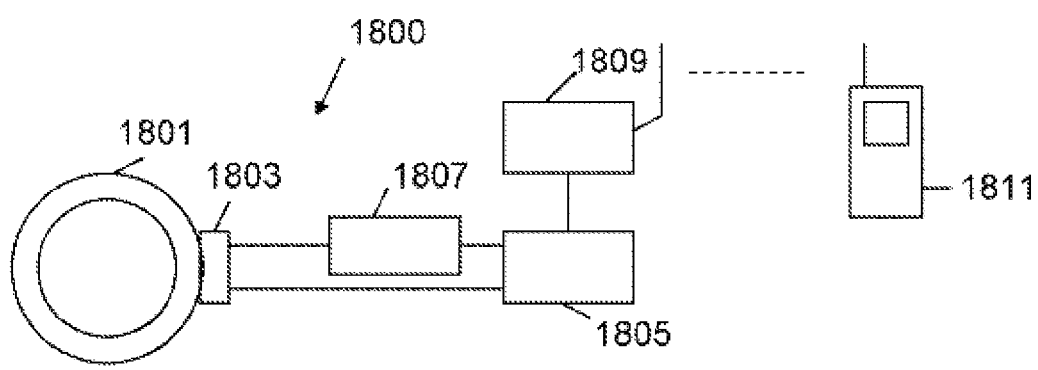
FIG. 18 shows a schematic block diagram of a detection device with a communication device.

FIG. 18 shows a schematic block diagram of a detection device 1800. The detection device 1800 has an armband 1801, a sensor array 1803 attached to the armband 1801, a microprocessor 1805, a microwave circuit 1807 for generating the transmission signals, and a communication device 1809.

By way of example, the sensor array 1803 has a microwave sensor, a temperature sensor and a moisture sensor.

By way of example, the microprocessor 1805 is configured like the processor 109 in FIG. 1.

The communication device 1809 is configured for providing a communication link between the detection device 1800 and a further communication device 1811. By way of example, the communication device 409 comprises a Bluetooth interface. By way of example, the further communication device 1811 is a mobile radio device, a smartphone or a GPS-based apparatus.

The measurements or detections of blood picture parameters can be provided in a reproducible fashion by an armband with a detection device of the aforementioned detection devices if the armband with the detection device is pressed against the arm during the measurements with a predetermined or prescribed contact pressure. In order to provide the predetermined contact pressure, the armband is equipped with a setting device in addition to the detection device. The setting device is configured in such a way that it can set the predetermined or prescribed contact pressure, at least when the blood picture parameter is being detected by the detection device.

The armband with the detection device and the setting device is configured to be applied to the arm of the patient, particularly in the region of his wrist.

In particular, this location of the wrist does not impair the freedom of movement of the patient. Furthermore, this location is already established for patients for conventional blood pressure measuring instruments. A further advantage in placing the armband on the wrist consists of the fact that the pulse is usually felt at this position, the skin is thin and hence sources of errors can be reduced. Furthermore, by pressing-on the armband during the detection of the blood picture parameter, air gaps are avoided, which could change a microwave-technical adjustment by the detection device. By pressing-on the armband with the predetermined contact pressure, the armband can match the anatomy of the respective patient.

By using the armband with the detection device and the setting device, the blood picture parameter can be monitored continuously. An example of such a blood picture parameter is—as explained above—the blood sugar concentration. As a result of the option of continuous monitoring of the blood sugar concentration, determining the delay time between taking up food and the increase in blood sugar is made possible. Furthermore, it is possible to react very quickly to variations in the daily routine of the patient. In particular, an alarm can be triggered in a timely fashion in the case of too much sugar or too little sugar.

In accordance with a further aspect, an armband is proposed, which has a detection device for detecting a blood picture parameter of blood in a blood vessel in the arm, and a setting device for setting a predetermined contact pressure of the armband on the arm. The detection device can have the features of the aforementioned detection devices.

In accordance with one embodiment, the measurement is carried out in a broadband fashion instead of in a narrowband fashion. By way of example, the transmission signals can be coupled into the blood vessel by means of a frequency sweep or as a partial signal of a broadband transmission signal. As a result of the preferred vectorial detection of the S-parameter, it is now possible to evaluate the complex relative permittivity and not only the real part thereof. By observing frequency shifts of a plurality of absorption lines, the blood picture parameter can be ascertained more accurately. This is preferably carried out by means of a two-port measurement and not by means of a one-port measurement.

Figure 19:
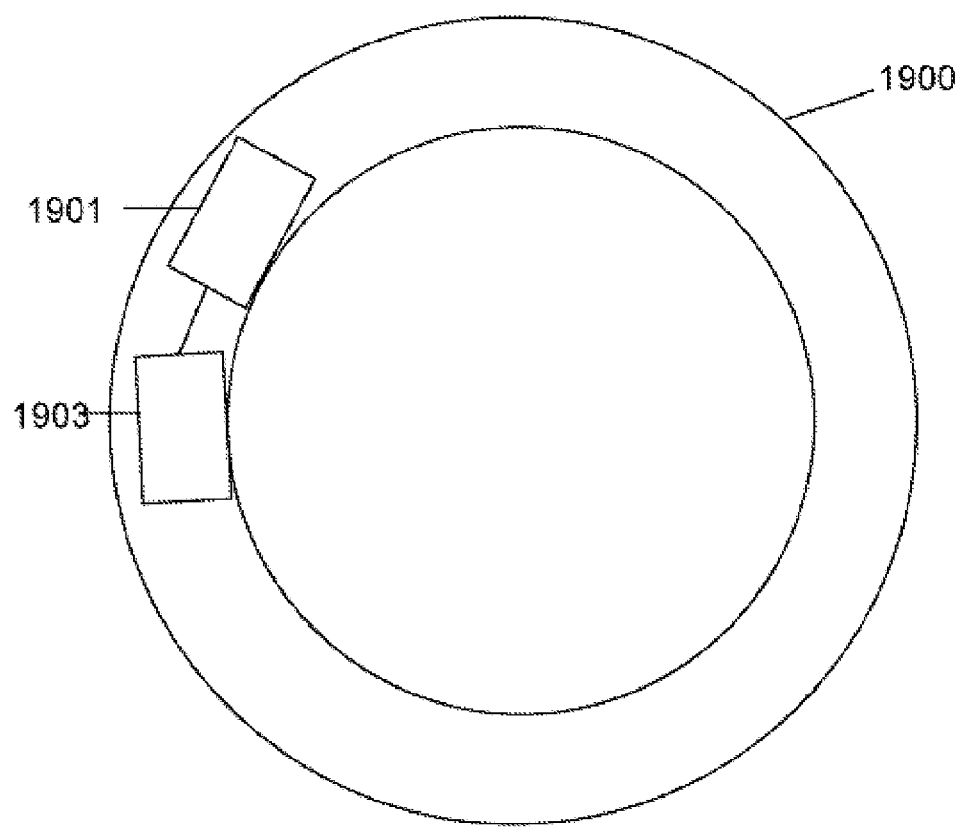
FIG. 19 shows a schematic block diagram of an armband.

FIG. 19 shows a block diagram of an exemplary embodiment of an armband 1900 with a detection device 1901 and a setting device 1903. The detection device 1901 is configured to detect a blood picture parameter of blood in a blood vessel of the arm. An example for the blood picture parameter to be detected is the glucose concentration in the blood.

The setting device 1903 is configured to set a predeterminable contact pressure of the armband 1900 on the arm. By setting the predetermined contact pressure of the armband 1900, the setting device 1903 can ensure reproducible detections of the blood picture parameter by the detection device 1901. To this end, the setting device 1903 is, in particular, configured to set the contact pressure of the armband 1900 to the predeterminable contact pressure when the blood picture parameter is being detected by the detection device 1901.

In particular, the armband 1900 is embodied as an inflatable armband 1900. Here, the setting device 1903 in particular has an air pump, which is configured to inflate the armband 1900 for setting the predetermined contact pressure.

In detail, the detection device 1901 comprises electrodes in particular, which are configured to couple at least a radiofrequency signal into the blood vessel. The radiofrequency signal is configured to supply a parameter for detecting the blood picture parameter. An example for such a parameter is formed by the relaxation time constant τ of the blood picture parameter. Here, the setting device 1903 is more particularly designed to set the contact pressure of the electrodes on the arm to the predetermined contact pressure.

Furthermore, the setting device 1903 can be embodied in such a way that it distributes the contact forces of the armband 1900 uniformly on the arm when the blood picture parameter is being detected by the detection device 1901. Furthermore, the setting device 1903 is preferably configured in such a way that it ensures uniform contact of the armband 1900 while the blood picture parameter is being detected by the detection device 1901.

Figure 20:
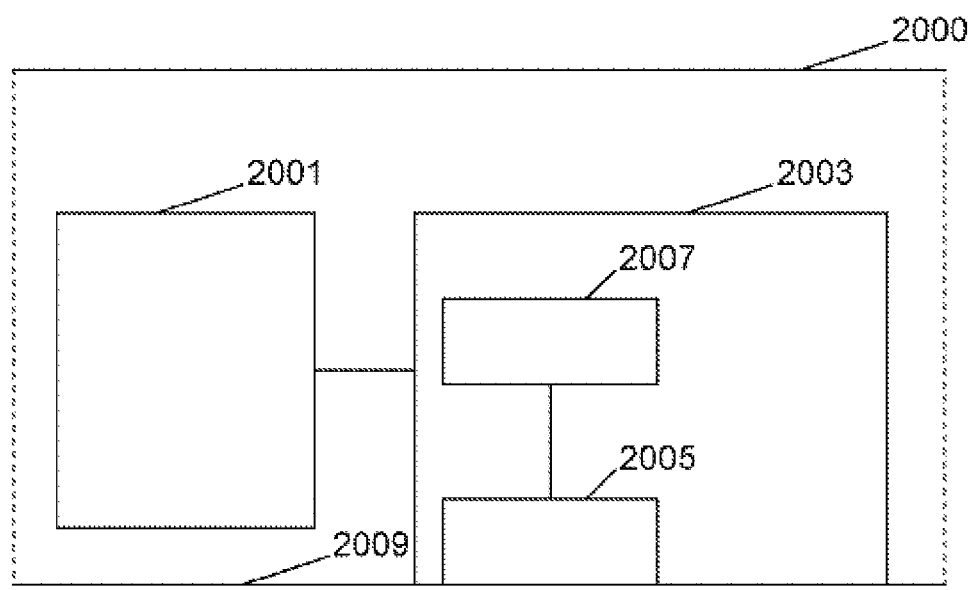
FIG. 20 shows a schematic block diagram of a section of an armband.

FIG. 20 shows a block diagram of a section of an exemplary embodiment of an armband 2000. The armband 2000 has a detection device 2001 and a setting device 2003. The detection device 2001 and the setting device 2003 are embodied at least like the detection device 1901 and the setting device 1903 of FIG. 19. Furthermore, the setting device 2003 of FIG. 20 has a sensor apparatus 2005 and a control apparatus 2007. The sensor apparatus 2005 is configured to measure a current contact pressure of the armband 2000 on the arm. Depending on the measured current contact pressure, the control apparatus 2007 sets the predetermined contact pressure on the arm.

Figure 21:
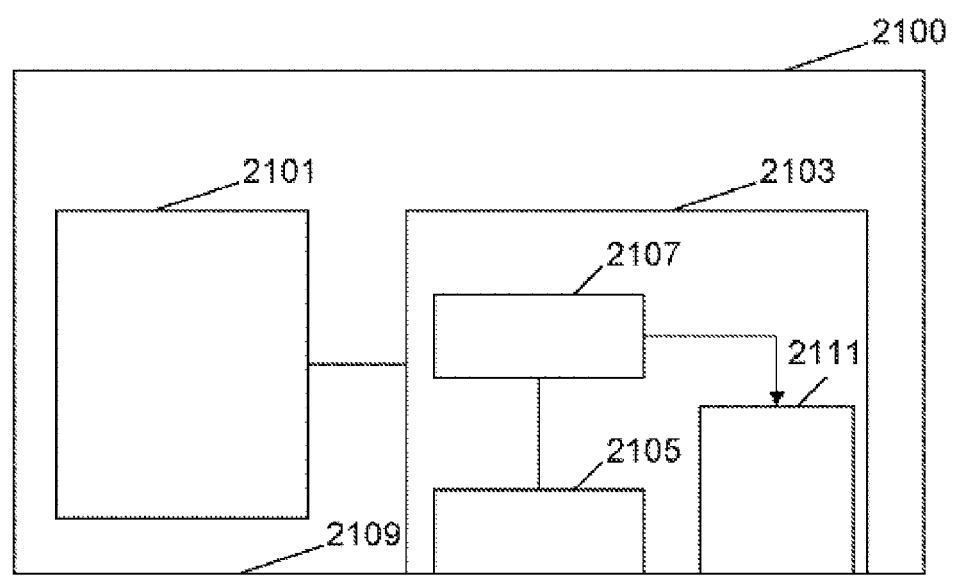
FIG. 21 shows a schematic block diagram of a section armband.

FIG. 21 shows a block diagram of a section of a further exemplary embodiment of an armband 2100. The armband 2100 has a detection device 2101 and a setting device 2103. The setting device 2103 has a sensor apparatus 2105, a control apparatus 2107 and an air pump 2111. The sensor apparatus 2105 measures a current contact pressure of the armband 2100 on the arm. The control apparatus 2107 provides a control signal depending on the measured current contact pressure. By means of the provided control signal, the air pump 2111 is controlled for inflating the armband 2100.

Figure 22:
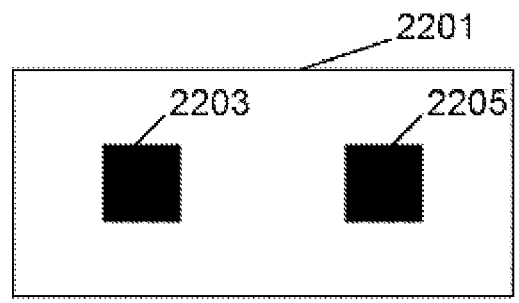
FIG. 22 shows a schematic block diagram of an arrangement of the electrodes of the detection device.

FIG. 22 illustrates a schematic block diagram of an arrangement 2200 of the electrodes, i.e. antennas 2203, 2205 of the detection device for detecting a blood picture parameter of blood in a blood vessel of the arm.

Without loss of generality, the arrangement 2200 only shows two electrodes 2203 and 2205. In particular, the arrangement 2200 is part of the detection device and, for example, embodied as a plate with exemplary dimensions of 5 cm by 2 cm. The electrodes 2203, 2205 for example have a base area of 5 mm by 5 mm. By way of example, the distance between the electrodes 2203, 2205 is 1 to 2 cm. This firstly obtains a strong enough transmission and secondly ensures a sufficiently deep penetration depth into the body.

The invention claimed is:

1. A detection device for detecting a blood picture parameter of blood in a blood vessel, comprising:
   a transmitter with a number of transmission antennas for emitting at least one transmission signal;
   a receiver with a number of reception antennas for receiving at least one reception signal;
   a processor configured to select a first detection configuration comprising one transmission antenna of the number of transmission antennas and one reception antenna of the number of reception antennas and to select a second detection configuration comprising one transmission antenna of the number of transmission antennas and one reception antenna of the number of reception antennas; and,
   a loss detector, which is configured,
   if the first detection configuration for emitting a transmission signal is selected, to detect a first loss variable on the basis of the transmission signal and a reception signal and,
   if the second detection configuration for emitting a transmission signal is selected, to detect to detect a second loss variable on the basis of the transmission signal and a reception signal; wherein
   the processor is configured to select the detection configuration with the smaller loss variable for detecting the blood picture parameter.

2. The detection device as claimed in claim 1, wherein,
   if the first detection configuration is selected, the transmitter is configured to emit the transmission signal by the transmission antenna of the first detection configuration, and wherein, if the first detection configuration is selected, the receiver is configured to receive the reception signal by the reception antenna of the first detection configuration, wherein,
   if the second detection configuration is selected, the transmitter is configured to emit the transmission signal by the transmission antenna of the second detection configuration, and wherein, if the second detection configuration is selected, the receiver is configured to receive the reception signal by the reception antenna of the first detection configuration, and wherein
   the loss detector is configured to detect the first loss variable on the basis of the transmission signal and the reception signal of the first detection configuration and to detect the second loss variable on the basis of the transmission signal and the reception signal of the second detection configuration.

3. The detection device as claimed claim 1, wherein the processor is configured to compare the first loss variable with the second loss variable to ascertain the smaller loss variable of the two loss variables.

4. The detection device as claimed in claim 1, further comprising a switching matrix, which switching matrix is configured to connect respectively one output of a reception antenna of the number of reception antennas with the loss detector.

5. The detection device as claimed in claim 4, wherein the switching matrix can be controlled by the processor.

6. The detection device as claimed in claim 1, wherein the transmitter comprises a transmission signal generator and an output of the transmission signal generator can be connected to respectively one transmission antenna of the number of transmission antennas by a switching matrix.

7. The detection device as claimed in claim 6, wherein switching matrix can be controlled by the processor.

8. The detection device as claimed in claim 1, wherein the transmitter is configured to emit transmission signals of the same frequency or of the same mode when using the first detection configuration and when using the second detection configuration.

9. The detection device as claimed in claim 8, wherein the transmitter is configured to emit transmission signals of the same frequency in a frequency range between 1 GHz and 15 GHz, when using the first detection configuration and when using the second detection configuration.

10. The detection device as claimed in claim 8, wherein the transmitter is configured to emit transmission signals of the same mode in a transverse electric mode or a transverse magnetic mode, when using the first detection configuration and when using the second detection configuration.

11. The detection device as claimed in claim 1, wherein the transmitter comprises at least two transmission antennas or wherein the receiver comprises at least two reception antennas.

12. The detection device as claimed in claim 11, wherein the antennas are dipole antennas, frame antennas, or patch antennas.

13. The detection device as claimed in claim 1, wherein the loss detector is a network analyzer.

14. The detection device as claimed in claim 13, wherein the loss detector is a vector or scalar network analyzer, or a power detector.

15. The detection device as claimed in claim 1, wherein, to detect the blood picture parameter,
- the transmitter is configured, using the transmission antenna of the selected detection configuration, to couple a first transmission signal with a first frequency and a second transmission signal with a second frequency into the blood vessel;
- the receiver is configured, using the reception antenna of the selected detection configuration, to receive a first reception signal at the first frequency and a second reception signal at the second frequency;
- the loss detector is configured to ascertain a first loss variable on the basis of the first transmission signal and the first reception signal at the first frequency and to ascertain a second loss variable on the basis of the second transmission signal and the second reception signal at the second frequency; and
- the processor is configured to ascertain a first frequency shift of the first loss variable relative to a first reference loss variable, to establish a second frequency shift of the second loss variable relative to a second reference loss variable, and to establish the blood picture parameter on the basis of the first frequency shift and the second frequency shift.

16. The detection device as claimed in claim 1, wherein, to detect the blood picture parameter,
- the transmitter is configured, using the transmission antenna of the selected detection configuration, to couple a first transmission signal with a first frequency and a second transmission signal with a second frequency into the blood vessel;
- the receiver is configured, using the reception antenna of the selected detection configuration, to receive a first reception signal at the first frequency and a second reception signal at the second frequency; and wherein
- the processor is configured to establish a first loss variable on the basis of the first transmission signal and the first reception signal, to establish a second loss variable on the basis of the second transmission signal and the second reception signal, to ascertain a relaxation time constant of a blood constituent depending on the frequency with the larger loss variable, and to establish the blood picture parameter on the basis of a pre-known relationship between the relaxation time constant and the blood picture parameter.

17. The detection device as claimed in claim 1, wherein the loss detector is configured, to ascertain the first loss variable and the second loss variable, to carry out a two-port measurement.

18. The detection device as claimed in claim 17, wherein the loss detector is configured, to ascertain in each case a forward transmission factor $S_{21}$ by the two-port measurement.

19. The detection device as claimed in claim 1, wherein the loss detector is configured to ascertain the first loss variable and the second loss variable respectively on the basis of the following formula:

$$P_{loss} = 1 - |S_{11}|^2 - |S_{21}|^2,$$

where $P_{loss}$ denotes the respective loss variable and where $S_{11}$ denotes the input reflection factor and $S_{21}$ denotes a forward transmission factor.

20. The detection device as claimed in claim 1, wherein the transmitter is configured to couple in the transmission signal as a mode or a wave type.

21. The detection device as claimed in claim 20, wherein the transmitter is configured to couple in the transmission signal as a transverse electric wave, a transverse magnetic wave, a transverse electromagnetic wave, or an HE wave.

22. The detection device as claimed in claim 20, wherein the transmitter is configured to couple in the transmission signal tangentially or transversely with respect to an extent of the blood vessel or with respect to a blood flow direction.

23. The detection device as claimed in claim 1, wherein the blood picture parameter is a concentration of a blood constituent.

24. The detection device as claimed in claim 23, wherein the blood constituent is a sugar or oxygen.

25. A method for detecting a blood picture parameter of blood in a blood vessel, using a transmitter with a number of transmission antennas for emitting at least one transmission signal and a receiver with a number of reception antennas for receiving at least one reception signal, comprising the following steps:
- selecting a first detection configuration comprising selection a transmission antenna of the number of transmission antennas and a reception antenna of the number of reception antennas;
- if the first detection configuration for emitting a transmission signal is selected, detecting a first loss variable on the basis of the transmission signal and a reception signal,
- selecting a second detection configuration comprising a transmission antenna of the number of transmission antennas and a reception antenna of the number of reception antennas;
- if the second detection configuration for emitting a transmission signal is selected, detecting a second loss variable on the basis of the transmission signal and a reception signal; and
- selecting the detection configuration with the smaller loss variable for detecting the blood picture parameter.

* * * * *

UNITED STATES PATENT AND TRADEMARK OFFICE
CERTIFICATE OF CORRECTION

| | | |
|---|---|---|
| PATENT NO. | : 9,028,408 B2 | Page 1 of 1 |
| APPLICATION NO. | : 13/884377 | |
| DATED | : May 12, 2015 | |
| INVENTOR(S) | : Georg Fischer | |

It is certified that error appears in the above-identified patent and that said Letters Patent is hereby corrected as shown below:

Claims
At Column 18, line 34, "claimed" should be --claimed in--.

Signed and Sealed this
Ninth Day of February, 2016

Michelle K. Lee
*Director of the United States Patent and Trademark Office*